United States Patent [19]

Takahama

[11] Patent Number: 4,549,318
[45] Date of Patent: Oct. 29, 1985

[54] PROSTHETIC DEVICE WITH A KNEE MECHANISM

[76] Inventor: Itsuro Takahama, 5-27-8, Hanazono, Kumamoto-shi, Kumamoto-ken, Japan

[21] Appl. No.: 696,190

[22] Filed: Jan. 29, 1985

[51] Int. Cl.⁴ .......................... A61F 1/04; A61F 1/08
[52] U.S. Cl. ..................................................... 623/44
[58] Field of Search ........................................ 3/22–29, 3/2

[56] References Cited

U.S. PATENT DOCUMENTS 3,863,274  2/1975  Glabiszewski ............................. 3/27
3,982,279  9/1976  Valenti et al. ............................. 3/27
4,215,441  8/1980  Wilson ................................... 3/27 X

FOREIGN PATENT DOCUMENTS 2023040  8/1971  Fed. Rep. of Germany ............ 3/26

Primary Examiner—Ronald L. Frinks
Attorney, Agent, or Firm—Fleit, Jacobson, Cohn & Price

[57] ABSTRACT

A prosthetic device comprising a knee mechanism including two discs of a large diameter, about the circumferential surfaces of which are disposed an upper and a lower gripping members to be frictionally engageable therewith so that a thigh element is firmly fastened with respect to a shank element to support the body weight of the user when the former is bent with respect to the latter.

2 Claims, 4 Drawing Figures

U.S. Patent
Oct. 29, 1985
4,549,318
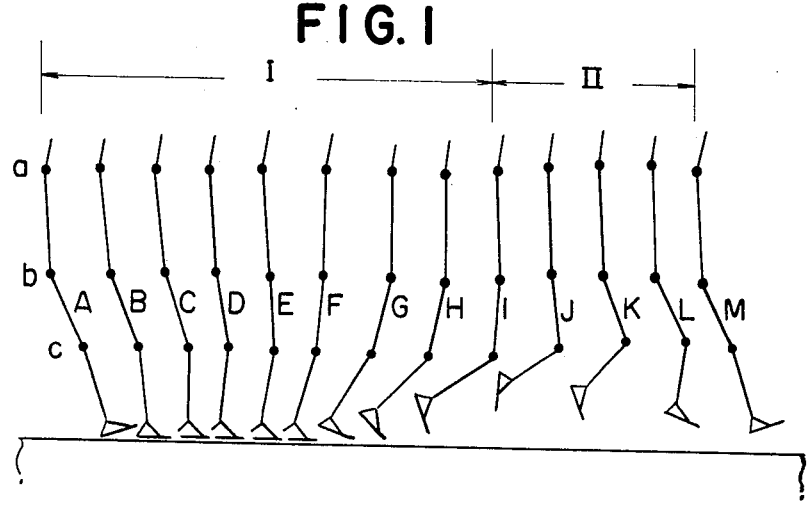
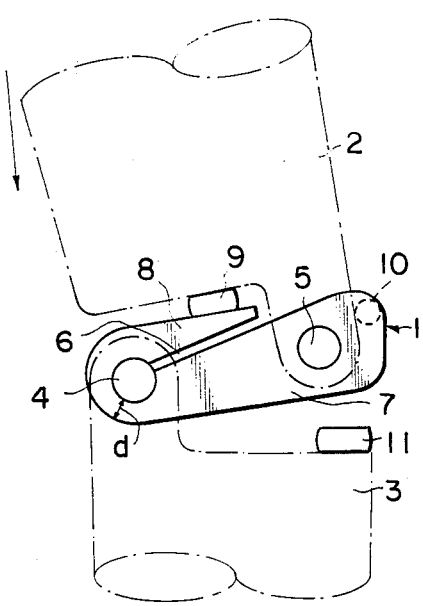
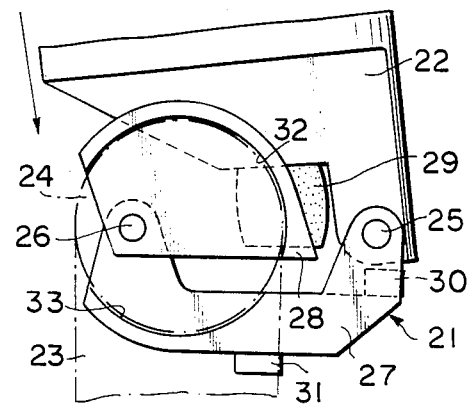
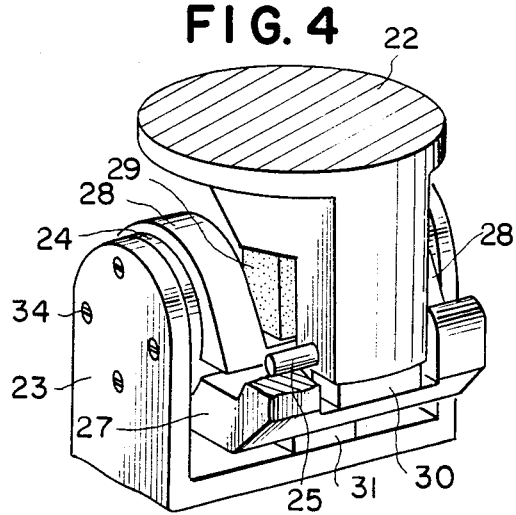

PROSTHETIC DEVICE WITH A KNEE MECHANISM

BACKGROUND OF INVENTION

This invention relates to a prosthetic device and more particularly to a prosthetic device comprising an improved knee mechanism.

A prosthetic device must be so designed that the user of the device can walk in a manner as closely as possible to the walking motion of a person with natural limbs, as illustrated in FIG. 1. As can be seen from the figure, walking is divided into two phases: a striding or weight-bearing phase (I) including stages A through H and a swing or non-weight-bearing phase (II) including stages I through M. At the initial stage of the weight-bearing phase (stage A), the body parts (a: neck, b: waist, c: knee) are well behind the foot while the thigh and the shank joinedly connected by the knee form a substantially straight line. As the foot comes into complete contact with the ground and the walking proceeds, the knee flexes (that is, the thigh and the shank bend with respect to each other) as at stages B through E, and then the heel of the foot begins to lift off the ground, as at stages F and G. At the time when the toe of the foot clears the ground (stage H), the striding or weight-bearing phase ends. During the non-weight-bearing phase (II), the walker swings the thigh forward about the groin and the shank forward about the knee (stages I through L) and the weight-bearing phase starts again when the heel of the foot contacts the ground (stage M).

Thus, in order to allow the user to simulate natural walking motion, a prosthetic knee mechanism jointedly connecting a thigh element and a shank element should be so designed that, in the striding or weight-bearing phase, it can absorb the shock produced by the contact of the foot device with the ground and also enable the thigh element and the shank element to bend sufficiently relative to each other while supporting the weight of the user (i.e. without causing knee buckling). Besides, such knee mechanism should be so constructed that the shank element can be swing freely in the non-weight-bearing phase.

A typical conventional prosthetic device including a knee mechanism is shown in FIG. 2. The device includes an element 1 for jointedly connecting a thigh element 2 and a shank element 3. The end portion, toward the back of the user of the device (the left side in the figure), of the joint element 1 is pivotably mounted about a horizontal shaft 4 to which the shank element 3 is secured. The thigh element 2 is pivotably mounted, about a horizontal shaft 5, on the other side (i.e. the front of the user) of the joint element 1. The thigh element 2 may be directly secured to the joint element 1. The joint element 1 is made of a relatively pliable material and is so configured that there is a gap 6 extending from the shaft 4 toward the front of the user, thus separating the joint element 1 into two parts 7 and 8. Between the thigh element and the joint element 1, there is provided a small spacer element 9 secured to the thigh element 2 or the upper surface of the joint element 1. Generally there are also provided a stopper 10 on the joint element 1 and a stopper 11 on the shank element 3.

In the swing or non-weight-bearing phase with such device the shank element 3 can swing forward since the joint element 1 is pivotably mounted about the shaft 4 to which the shank element is secured. The forward swing movements of the thigh element 2 and the shank element 3 are restricted by the stopper 10 and the stopper 11, respectively, so that the thigh element 2 and the shank element 3 form a substantially straight line.

In walking with the prosthetic device to simulate the striding or non-weight-bearing phase, particularly such stages as B through E where the knee flexes, the load of the body weight of the user acts behind the shaft 4 serving as a knee joint, as shown by the arrow in FIG. 2, and hence rotates the thigh element 2 backward (i.e. anti-clockwise in the figure) about the shaft 4, thus lifting the part 7 of the joint element 1 while pressing down the part 8 of the joint element 1 through the spacer element 9. As a result, the element 1 clamps the shaft 4 to which the shank element 3 is secured, so that the thigh element 2 is fastened with respect to the shank element. Thus, the intension is that the prosthetic device can support the body weight of the user, with the thigh element 2 and the shank element 3 being bent relative to each other.

However, such conventional prosthetic device has a drawback in that there is produced only a relatively small moment about the shaft 4 by the joint element 1 to clamp the shaft 4, since said shaft is of a small diameter. Thus, with such device there sometimes occurs knee buckling, i.e. the user sometimes falls backward because of the failure of the device to support the body weight. It may be considered that the clamping force can be increased by enlarging the diameter of the shaft. However, this would rather result in a practical disadvantage since the strength of the joint element 1 would be decreased because of reduction of the width between the shaft and the joint element (d in FIG. 2). The conventional prosthetic device as illustrated is also weak in strength in view of the requirement that the joint element 1 be made of a pliable material to serve as a clamp about the shaft 4. Accordingly, as a matter of fact, the user of such a device must walk in such a manner that the thigh element and the shank element bend as little as possible with respect to each other in order to avoid knee buckling or breakage of the device. Such walking is quite dissimilar to the walking motion of a person with natural limbs as illustrated in FIG. 1. Besides, the conventional prosthetic device as illustrates has less cushioning effect for absorbing the shock from the contact of the device with the ground. This is because the construction of the device limits the provision of a cushioning element to a small element such as the spacer 9.

SUMMARY OF INVENTION

The principal object of the present invention is to overcome the above-mentioned drawbacks and to provide a prosthetic device including a knee mechanism producing a higher force to secure a thigh element and a shank element to each other under the bended condition and having a higher cushioning effect.

Thus, according to the present invention, there is provided a prosthetic device comprising a thigh element, a shank element and a knee mechanism for jointedly connecting the thigh element and the shank element, in which the knee mechanism includes two discs of a large diameter disposed at the opposite sides of the thigh element and secured to the shank element. The knee mechanism also includes an upper gripping member including two arcuate surfaces of a diameter slightly larger than that of the discs and disposed around the upper circumferential surfaces of the discs, and a lower gripping member including two arcuate surfaces of a diameter slightly larger than that of the discs and disposed around the lower circumferential surfaces of the discs. The upper gripping member and lower gripping member are pivotably interconnected about a horizontal axis toward the back of the user of the prosthetic device. Further, the thigh element is pivotably connected to the lower gripping member about a horizontal axis toward the front of the user. Thus, the arrangement is such that, when the thigh element pivots backwards with respect to the user, it presses the upper gripping member downwards and lifts up the lower gripping member for frictional engagement of the arcuate surfaces of these gripping members with said discs.

With the prosthetic device of the present invention of such construction, a very large force can be produced for fastening the thigh element with respect to the shank element, since the gripping members frictionally engage with the discs of a large diameter producing a large frictional force. Thus, the prosthetic device according to the present invention can sufficiently support the weight of the user without knee buckling, even when the thigh element is bent by a large angle with respect to the shank element. In addition, the configuration of the prosthetic device of the present invention, where the discs of a large diameter are employed, leaves a large space in the knee mechanism while producing a large fastening force. By providing a resilient material in such space, there can be obtained a prosthetic knee mechanism with a high cushioning containing effect. Thus, in a preferred embodiment of the device according to the present invention, there is provided a resilient material of large volume between the thigh element and the upper gripping member so that said thigh element presses said upper gripping member downwards through said resilient material.

DESCRIPTION OF THE EMBODIMENT WITH REFERENCE TO THE DRAWING

The above-mentioned and other features of the present invention will be more fully understood from the following description of the preferred embodiment with reference to the drawing, in which:

FIG. 1 illustrates a typical walking motion of a normal person.

FIG. 2 is a side view of a typical conventional prosthetic device.

FIG. 3 is a cross sectional side view of a preferred embodiment of the prosthetic device of the present invention.

FIG. 4 is a partially cut-away perspective view of the device of FIG. 3.

The prosthetic device of the present invention as illustrated in FIGS. 3 and 4 overcomes the drawbacks of the conventional prosthetic device as illustrated in FIG. 2 and enables the user to closely simulate the walking motion as shown in FIG. 1.

In the embodiment of the present invention as illustrated in FIGS. 3 and 4, the prosthetic device includes a novel knee mechanism, generally indicated as 21, for jointedly connecting a thigh element 22 and a shank element 23. The knee mechanism 21 includes two discs 24 (in the figures, only one disc can be seen) disposed at the opposite sides of the thigh element 22. As can be seen, the discs 24 have a relatively large diameter and are secured to the shank element 23 through a suitable fastening means such as bolts 34.

The knee mechanism further includes a gripping member 27. The gripping member 27 has two arcuate portions at the opposite sides of the thigh element, so that there are formed two arcuate surfaces 33 with a diameter slightly larger than that of the discs 24. Thus, the arcuate surfaces 33 at the opposite sides of the thigh element 22 are disposed around the lower circumferential surfaces of the discs at the opposite sides of the thigh element 22. The knee mechanism further includes a gripping member 28. This gripping member 28 also has two arcuate surfaces 32 having a diameter slightly larger than that of the discs, so that the two arcuate surfaces 32 are disposed around the upper circumferential surfaces of the two discs at the opposite sides of the thigh element 22. The upper gripping member 28 is depressed at its central part so as to form a large space for providing a resilient material 29.

The upper gripping means 28 and the lower gripping means 27 are pivotably interconnected about a horizontal axis 26 toward the back of the user of the device (the left side, in FIG. 3). The thigh element 22 is pivotably connected to the lower gripping member about a horizontal axis 25 toward the front of the user of the device. There is mounted on the lower gripping member 27 a stopper 30 for restricting forward movement of the thigh element 22. There is also provided a stopper 31 on the lower surface of the lower gripping member 27. The stopper 31 serves to restrict the downward movement of the lower gripping member 27, through the contact with the shank element 23. As described above, between the upper gripping member 28 and the thigh element 22, it is preferable to provide a resilient material 29 of large volume.

Thus, when the thigh element 22 pivots backwards with respect to the user of the device, due to his body weight (as shown by the arrow in FIG. 3), the thigh element 22 presses the upper gripping member 28, preferably through the resilient material 29, while it lifts up the lower gripping member 27. As a result, the arcuate surfaces 32,33 of the gripping members 28,27 frictionally engage with the discs 24 to grip them, where the gripping powers are very large because there produce high moments about the discs with the large diameter secured to the shank element. The prosthetic device of the present invention as illustrated can thus support the weight of the user without knee buckling, with the thigh element being angled with respect to the shank element in order to simulate the striding or weight-bearing phase of the walking motion with natural limbs. The resilient material 29 of large volume imparts a high cushioning effect with the prosthetic device, in the striding phase. As will be understood, the mechanical strength of the prosthetic device is high since there is no requirement that the knee mechanism be composed of a pliable material.

In the swing or non-weight-bearing phase, the gripping members, the discs and the shank element are suspended about the shaft 25 with the gripping members being freely movable with respect to the discs secured to the shank element. Thus, the user of the prosthetic device can swing the thigh element 22 and the shank element 23 within the restriction by the stoppers 30 and 31.

What is claimed is:

1. A prosthetic device comprising a thigh element, a shank element and a knee mechanism jointedly connecting said elements, the knee mechanism including two discs having a large diameter disposed at the opposite sides of the thigh element and secured to the shank element, an upper gripping member including two arcuate surfaces of a diameter slightly larger than that of said discs and disposed around the upper circumferential surfaces of said discs, and a lower gripping member including two arcuate surfaces of a diameter slightly larger than that of said discs and disposed around the lower circumferential surfaces of said discs, said upper and lower gripping members being pivotably interconnected about a horizontal axis toward the back of the user of the prosthetic device, said thigh element being pivotably connected to said lower gripping member about a horizontal axis toward the front of the user, so that, when said thigh element pivots backwards with respect to the user, it presses the upper gripping member downwards and lifts up the lower gripping member for frictional engagement of said arcuate surfaces of these gripping members with said discs.

2. The prosthetic device as claimed in claim 1 in which there is provided a resilient material of large volume between the thigh element and the upper gripping member so that said thigh element presses said upper gripping member downwards through said resilient material.

* * * * *